(12) United States Patent
Weinmann

(10) Patent No.: US 7,958,994 B2
(45) Date of Patent: Jun. 14, 2011

(54) DEVICE FOR DISPOSAL OF AN ARTICLE OF PERSONAL HYGIENE

(76) Inventor: Gerold Weinmann, Welver (DE)

( * ) Notice: Subject to any disclaimer, the term of this patent is extended or adjusted under 35 U.S.C. 154(b) by 922 days.

(21) Appl. No.: 11/003,962

(22) Filed: Dec. 3, 2004

(65) Prior Publication Data

US 2005/0263575 A1   Dec. 1, 2005

(30) Foreign Application Priority Data

Jun. 1, 2004 (DE) .......................... 10 2004 026 954
Aug. 20, 2004 (DE) .......................... 10 2004 040 463

(51) Int. Cl.
*B65D 6/00* (2006.01)

(52) U.S. Cl. ........ 206/233; 206/494; 221/287; 221/102; 221/46

(58) Field of Classification Search .................. 206/440, 206/124, 233, 494, 536, 23.4, 826, 122.1, 206/125.4, 38, 820, 125, 438; 229/122.1, 229/125, 197; 211/22, 229, 46, 287, 49; 220/495.11, 908, 908.1, 908.2, 908.3, 909, 220/910, 911; 221/22, 229, 46, 287, 49, 221/102

See application file for complete search history.

(56) References Cited

U.S. PATENT DOCUMENTS

| | | | |
|---|---|---|---|
| 2,841,275 A * | 7/1958 | Schwimmer et al. | 206/233 |
| 2,915,218 A | 12/1959 | Roseman et al. | |
| 3,038,473 A | 6/1962 | Ladd | |
| 3,208,587 A * | 9/1965 | Lizio | 206/440 |
| 3,245,580 A * | 4/1966 | Campanella | 221/34 |
| 3,860,304 A * | 1/1975 | Bolton | 206/438 |
| 4,046,243 A * | 9/1977 | Valentine | 194/239 |
| D278,295 S * | 4/1985 | Thompson | D6/518 |
| 4,564,108 A * | 1/1986 | Widlund et al. | 206/438 |
| D290,227 S * | 6/1987 | Zutler | D9/652 |
| 4,750,640 A * | 6/1988 | Kobeck et al. | 221/186 |
| 4,879,442 A * | 11/1989 | Giovine | 206/233 |
| 5,050,742 A * | 9/1991 | Muckenfuhs | 206/494 |
| 5,286,538 A * | 2/1994 | Pearlstein et al. | 428/34.2 |
| 5,531,325 A * | 7/1996 | Deflander et al. | 206/494 |
| 5,622,281 A * | 4/1997 | Annand | 221/48 |
| 5,678,727 A * | 10/1997 | Rice | 221/98 |
| 6,263,814 B1 * | 7/2001 | O'Connor | 112/401 |
| 6,349,849 B1 * | 2/2002 | Pehr | 221/33 |
| 6,702,147 B2 * | 3/2004 | Ashford | 221/34 |
| 6,769,565 B2 * | 8/2004 | Tramontina et al. | 221/45 |
| 6,799,695 B1 * | 10/2004 | Borrero | 206/467 |

(Continued)

FOREIGN PATENT DOCUMENTS

DE    100 61 670 A1    6/2002

(Continued)

*Primary Examiner* — J. Gregory Pickett
*Assistant Examiner* — Andrew Perreault
(74) *Attorney, Agent, or Firm* — Alan G. Gorman; Barnes & Thornburg LLP

(57) ABSTRACT

The invention relates to a device for receiving an article of personal hygiene to be disposed of, especially a sanitary tampon, comprising a receptacle (1) made of recycling material and formed with a hold space (3) for the article and a storage space (4) for packings (14) which is separate from the hold space (3) and takes up the article for disposal, a wall (9) of the receptacle (1) being formed with a dump opening (6) adapted to be closed and through which the article can be thrown into the hold space (3), and with a withdrawal opening through which the packings can be taken out.

16 Claims, 5 Drawing Sheets

U.S. PATENT DOCUMENTS

| | | | |
|---|---|---|---|
| 6,830,151 B2 * | 12/2004 | Spencer et al. | 206/499 |
| 6,886,714 B2 * | 5/2005 | Kruchoski et al. | 221/48 |
| 7,004,313 B2 * | 2/2006 | Mitchell et al. | 206/213.1 |
| 7,147,129 B1 * | 12/2006 | Menefield | 206/440 |
| 7,293,738 B2 * | 11/2007 | Grebonval et al. | 242/597.7 |
| 7,357,274 B2 * | 4/2008 | Hewett | 221/35 |
| 7,410,052 B2 * | 8/2008 | Cook et al. | 206/233 |
| 2003/0178436 A1 * | 9/2003 | Ashford | 221/33 |
| 2005/0150801 A1 * | 7/2005 | Tippey | 206/440 |

FOREIGN PATENT DOCUMENTS

WO  WO 02/17844  3/2002

* cited by examiner

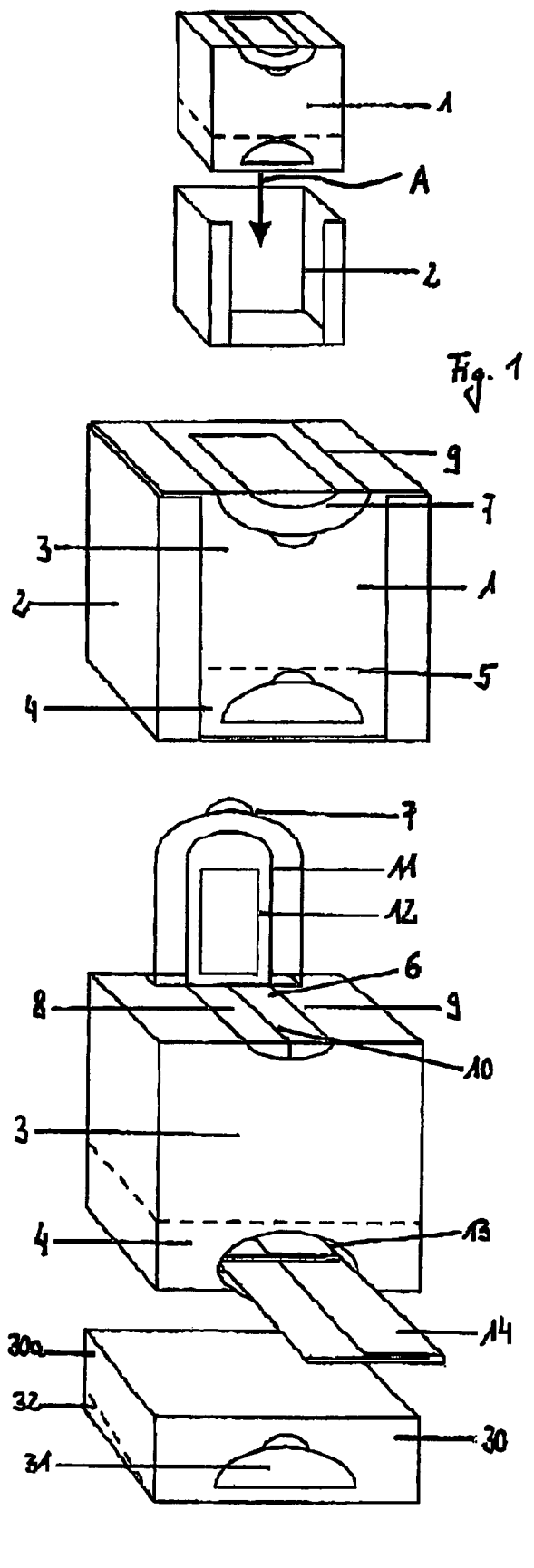

DEVICE FOR DISPOSAL OF AN ARTICLE OF PERSONAL HYGIENE

The invention relates to a device for receiving an article of personal hygiene to be disposed of, especially a sanitary tampon.

Devices of that kind are used to receive in particular disposable articles of personal hygiene to be disposed of after use. Such disposable articles of personal hygiene, for instance, are sanitary tampons. The articles in question not only must be kept hygienically and inodorous until their final disposal. There also is need for the device to lend itself to easy handling.

It is, therefore, an object of the invention to indicate a device for receiving an article of personal hygiene to be disposed of, permitting hygienic manipulation of the article to be disposed of and convenient to be handled by the user. Moreover, it is an object of the invention to provide a device which is inexpensive to produce.

These objects are met, in accordance with the invention, by a device for receiving an article of personal hygiene to be disposed of, especially a sanitary tampon, comprising a receptacle made of recycling material and formed with a hold space for the article and a storage space for packings which is separate from the hold space and takes up the article for disposal, a wall of the receptacle being formed with a dump opening adapted to be closed and through which the article can be thrown into the hold space, and with a withdrawal opening through which the packings can be taken out.

Such a device, on the one hand, offers an intermediate storage possibility for a used article of personal hygiene in the hold space until its final disposal. On the other hand, a storage space is provided in the receptacle, separate from the hold space. And this may be used to store packings into which the article to be disposed of may be put prior to dumping it in the hold space. In this manner the standard of hygiene is improved as the article to be disposed of will be enclosed in the packing when in the hold space. At the same time, odorous annoyance is avoided at the place where the device is located. Actually, an integrated solution is provided, both for receipt of the article of personal hygiene to be disposed of and for offering packings for that article, and it may be placed at any desirable location.

In a convenient modification of the invention, a lid is provided to close and open the dump opening by being swung into closed and open positions, respectively. The lid may be made of plastics. When not in use, the lid will cover the dump opening so as to close the hold space with articles for disposal inside it.

Optimum closing effect is obtained, with a preferred embodiment of the invention, in that in its closed position the lid will adhere to the wall of the receptacle. That may be achieved, for instance, by continuous or dot-wise application of an adhesive substance on an inner side of the lid facing the dump opening and/or on the outer surface of the wall of the receptacle opposite the inner side of the lid.

For better prevention of odorous annoyance, a fragrant substance is disposed on the lid, in a modification of the invention, so as to produce a smell of freshness. The fragrant substance, for example, may be a piece of fleece soaked with a deodorant.

The level of hygiene also may be improved by covering the dump opening with a cover formed with a slit. In this manner the dump opening may be concealed by the cover and the escape of odors from the hold space prevented by the cover.

It is advantageous to define the cover by strips of resilient material which are fastened to the wall of the receptacle and overlap in the range of the slit. This is a simple way of obtaining a cover which can be made to conceal from view the packed article of personal hygiene to be disposed of and yet allow convenient dumping thereof in the hold space. According to a modification of the invention, the strips may be strips of sheet material and thus fulfill the need for a material which meets standards of hygiene.

It is provided, with a preferred embodiment, that the receptacle be arranged releasably in an outer packing to assure the positioning of the receptacle with its hold and storage spaces. The outer packing may be used to place the receptacle in an upright position or hang it in a desired place, such as in a toilet. The outer packing may be made, for example, of stainless steel or plastics, in fashionable design, thus allowing the rather simple and inexpensive make of the receptacle to be covered up. Besides, the outer packing permits the receptacle to be adapted in appearance to the location where it is used, for instance, to a particular coloring of the wall tiles.

In a preferred further development of the invention, fresh articles of personal hygiene are offered in an additional storage space for such articles, separate from the hold and storage spaces. The further storage space is formed conveniently in another receptacle which is separate from the receptacle and may be arranged releasably in the outer packing. In this manner, the receptacle including the hold and storage spaces may be exchanged while the other storage receptacle with fresh articles of personal hygiene continues to be used as long as there are fresh articles of personal hygiene in the storage space, whereas the hold space already is completely filled with used articles to be disposed of. Alternatively, the additional storage space may be formed in the receptacle.

A convenient further development of the invention allows comfortable withdrawal of fresh articles of personal hygiene by the design of the storage space with a bottom which is inclined towards an aperture. Thereby, any fresh articles of personal hygiene remaining in the storage space always will slide towards the aperture to be grasped readily by a user.

Inexpensive manufacture and environmentally friendly disposal are enhanced by a preferred embodiment of the invention in that the receptacle and/or additional receptacle are made of cardboard or composite material. Such cardboard or composite material may be coated, for instance, with a liquid-repellant coat, at least in the area of interior walls of the hold space to further improve the standard of hygiene.

It is convenient to have a plurality of packings stored in the storage space for successive individual withdrawal. One or more packings thus may be removed, as desired. Adjacent ones of the plurality of packings may be interconnected releasably, as is known, for example, with plastics bags in a roll or in folded condition. The plurality of packings are plastic bags to further assist improving hygienic conditions.

The dump opening may be provided in the area of a top covering surface of the receptacle or at a front side of the receptacle. Provision of the dump opening in the area of the top covering surface of the receptacle offers the advantage of easier manipulation, i.e. dumping of the article to be disposed of and opening and closing of the lid for the dumping opening. Providing the dump opening at the front of the receptacle has the advantage that with this embodiment the dump opening can be disposed below the withdrawal opening.

The invention will be described further, by way of example, with reference to the accompanying drawings, in which:

FIG. 1 shows a receptacle and an outer packing to receive the receptacle;

FIG. 2 shows the receptacle according to FIG. 1 when positioned in the outer packing;

FIG. 3 shows the receptacle according to FIG. 1 with a lid in open position and with an additional receptacle for fresh articles of personal hygiene;

Figure 4A:
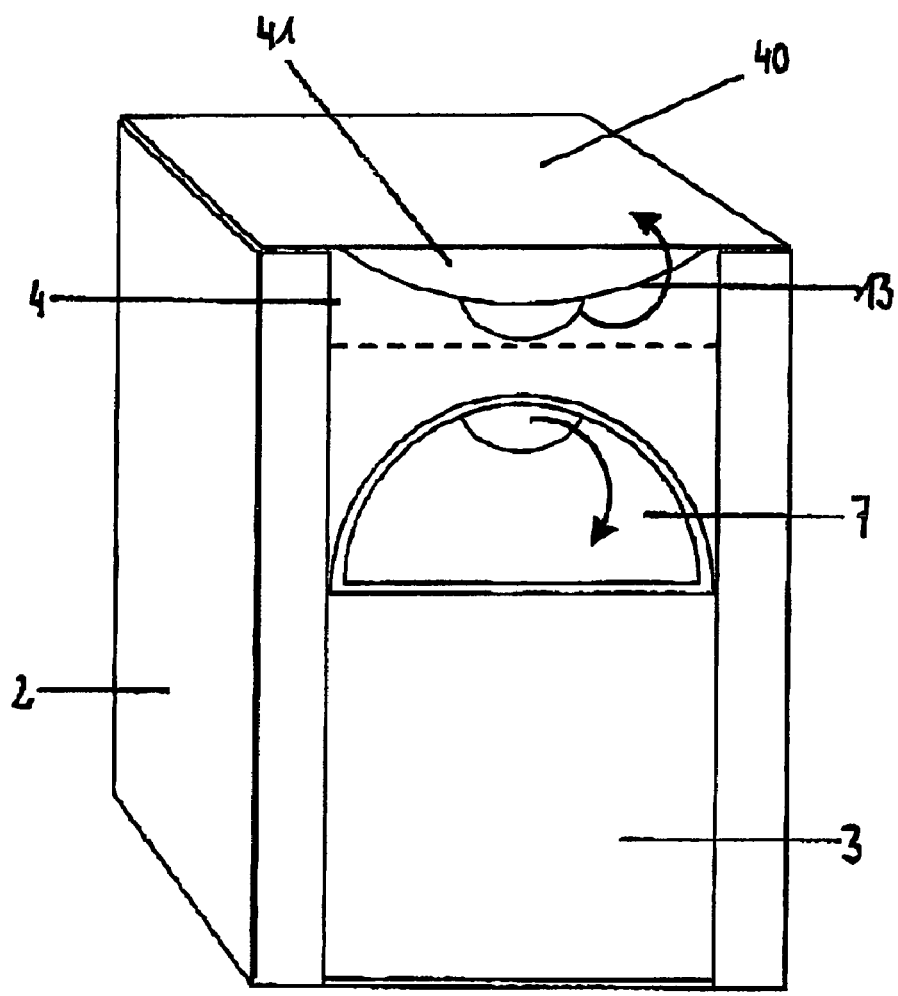
FIG. 4A shows another embodiment of a receptacle in an outer packing.

FIG. 1 is a perspective illustration of a receptacle 1 and an outer packing 2 for taking up the receptacle, as indicated diagrammatically by arrow A. The outer packing 2 serves the purpose of placing the receptacle 1 at the desired location, for instance, in a bathroom or toilet, either in upright position or hanging on the wall. To this end, the outer packing 2 may be made, for example, of stainless steel or plastics and may be given a fashionable design.

FIG. 2 shows the receptacle 1 according to FIG. 1 in perspective view. The receptacle 1 is formed with a hold space 3 and a storage space 4, the two being separated by a partioning bottom 5. The hold space 3 is destined to receive used articles of personal hygiene, such as sanitary tampons or diapers which are thrown through a dump opening 6 (see FIG. 3) into the hold space 3. In the presentation of FIG. 2 the dump opening 6 is closed by a lid 7.

FIG. 3 is a perspective view of the receptacle shown in FIG. 1, with the lid 7 in open position. In the area of the dump opening 6 film strips 8 are glued to the inside of a wall 9 of the receptacle 1. The film strips 8 overlap in the zone of a slit 10 through which the articles of personal hygiene to be disposed can be introduced into the hold space 3.

A piece of fleece 12 soaked with deodorant is arranged at the underside 11 of the lid 7.

The storage space 4 is formed below the hold space 3, being accessible from outside through a withdrawal opening 13. A packing 14 may be pulled out through the withdrawal opening 13, then a used article of personal hygiene to be disposed of is put inside prior to being dumped in the hold space 3. The packing 14, for instance, is a plastic bag which may be made of an opaque plastic material. A plurality of packings of the same kind are stored in the storage space 4, and they may be withdrawn individually, as required, through the withdrawal opening 13. The packings stored in the storage space 4 are interconnected in such a way that a packing, when being removed, will separate easily from the remaining packings in the storage space 4, such as along connecting points between edges of plastic bags.

FIG. 3 further illustrates another receptacle 30, including another storage space 30a as a reservoir for fresh articles of personal hygiene. Such a fresh article may be removed through an aperture 31. The additional receptacle 30 includes a bottom 32 which is inclined towards the aperture 31 so that fresh articles of personal hygiene can be taken out conveniently.

Figure 4B:
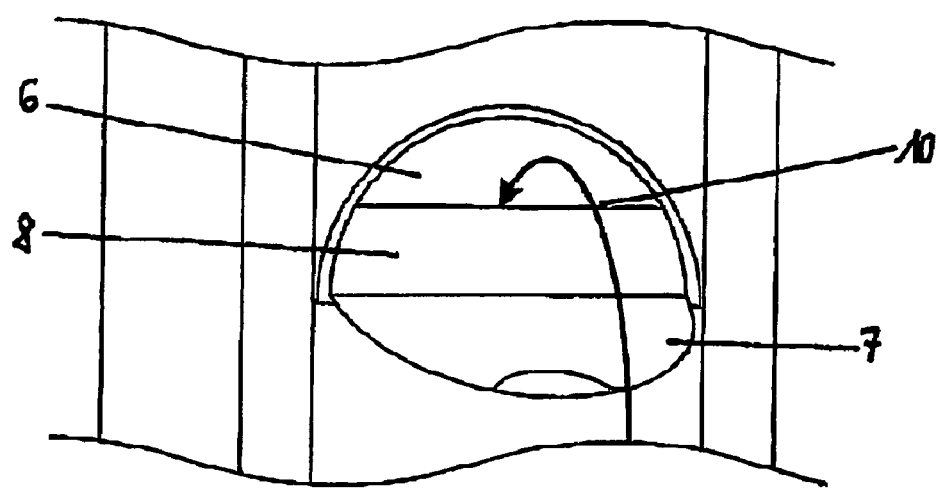
FIG. 4B is a partial view of the receptacle shown in FIG. 4A.

FIG. 4 is a perspective illustration of another embodiment of a receptacle 40 for receiving an article of personal hygiene to be disposed of. In FIG. 4 like features are designated by like reference numerals as in FIGS. 1 to 3. A dump opening 6 is formed at a front side of the receptacle 40 and below the withdrawal opening 13 for the packings, adapted to be closed by a lid 41. As may be gathered from FIG. 4B, which shows a section of the receptacle 40 according to FIG. 4A, the dump opening 6 again is covered by film strips 8.

Figure 5:
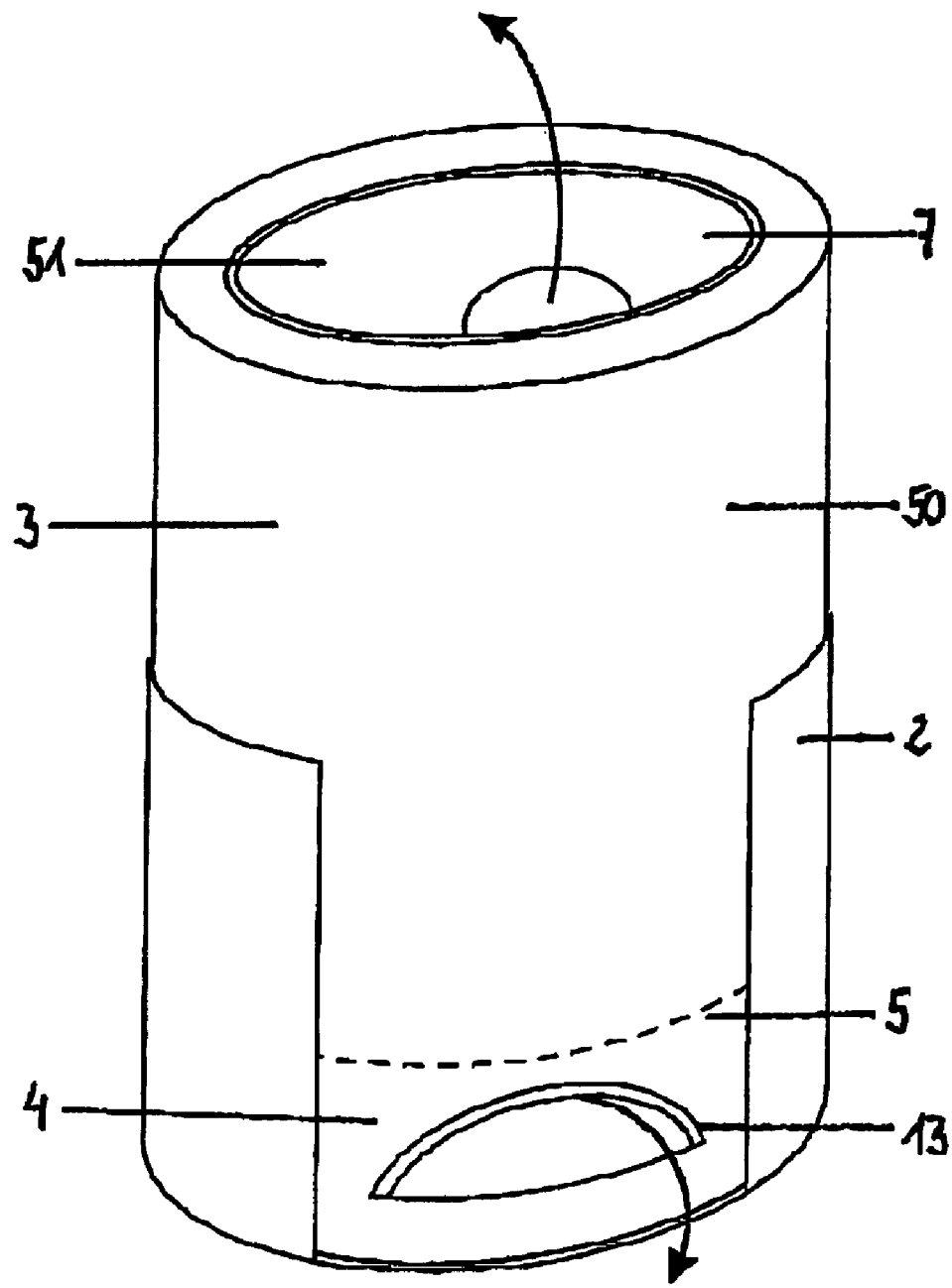
FIG. 5 shows another embodiment of a receptacle in an outer packing.

FIG. 5 shows another embodiment of a receptacle 50 for receiving an article of personal hygiene to be disposed of. In FIG. 5 like features are designated by like reference numerals as in FIGS. 1 to 3. In the embodiment illustrated in FIG. 5 the lid 7 which covers the dump opening 6 is arranged in the area of a top covering surface 51 of the receptacle 50. The storage space 4 is located below the hold space 3.

Figure 6A:
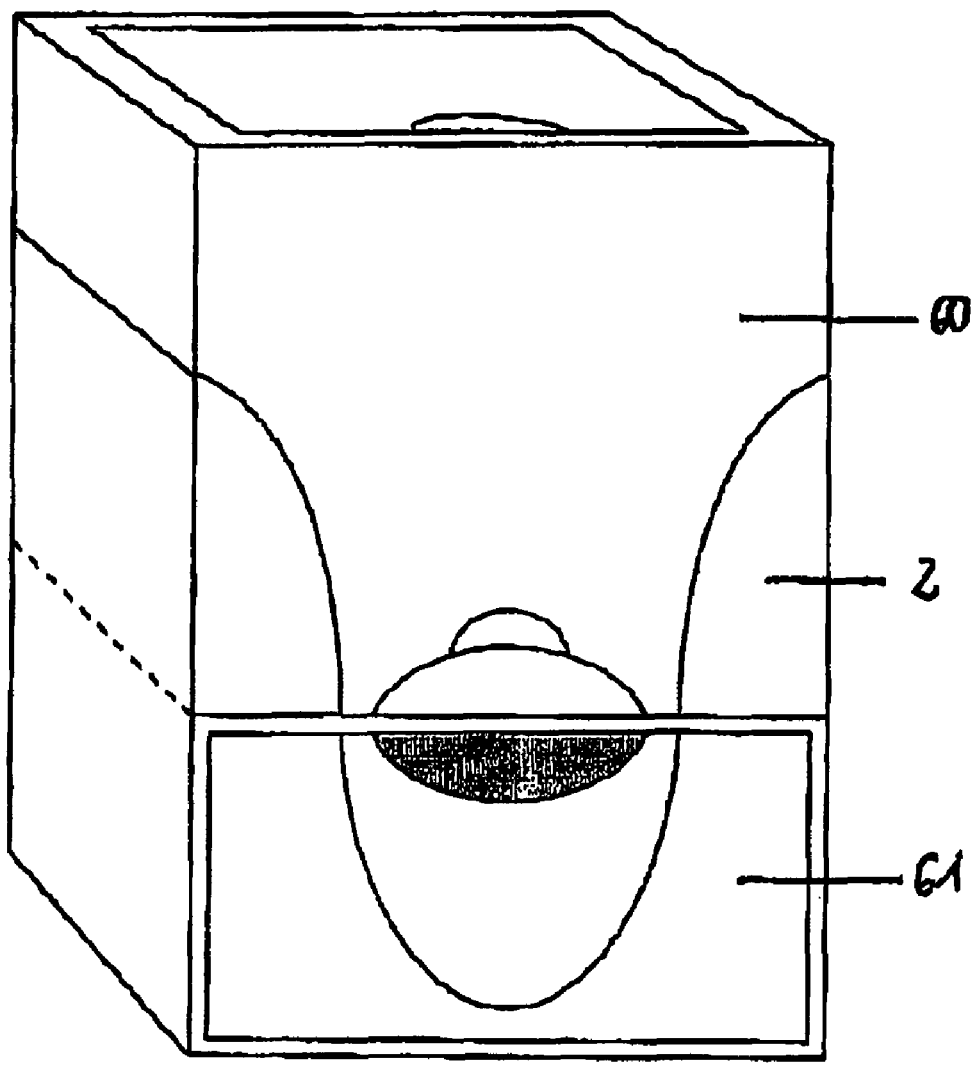
FIG. 6A shows a receptacle in an outer packing with a drawer compartment.
Figure 6B:
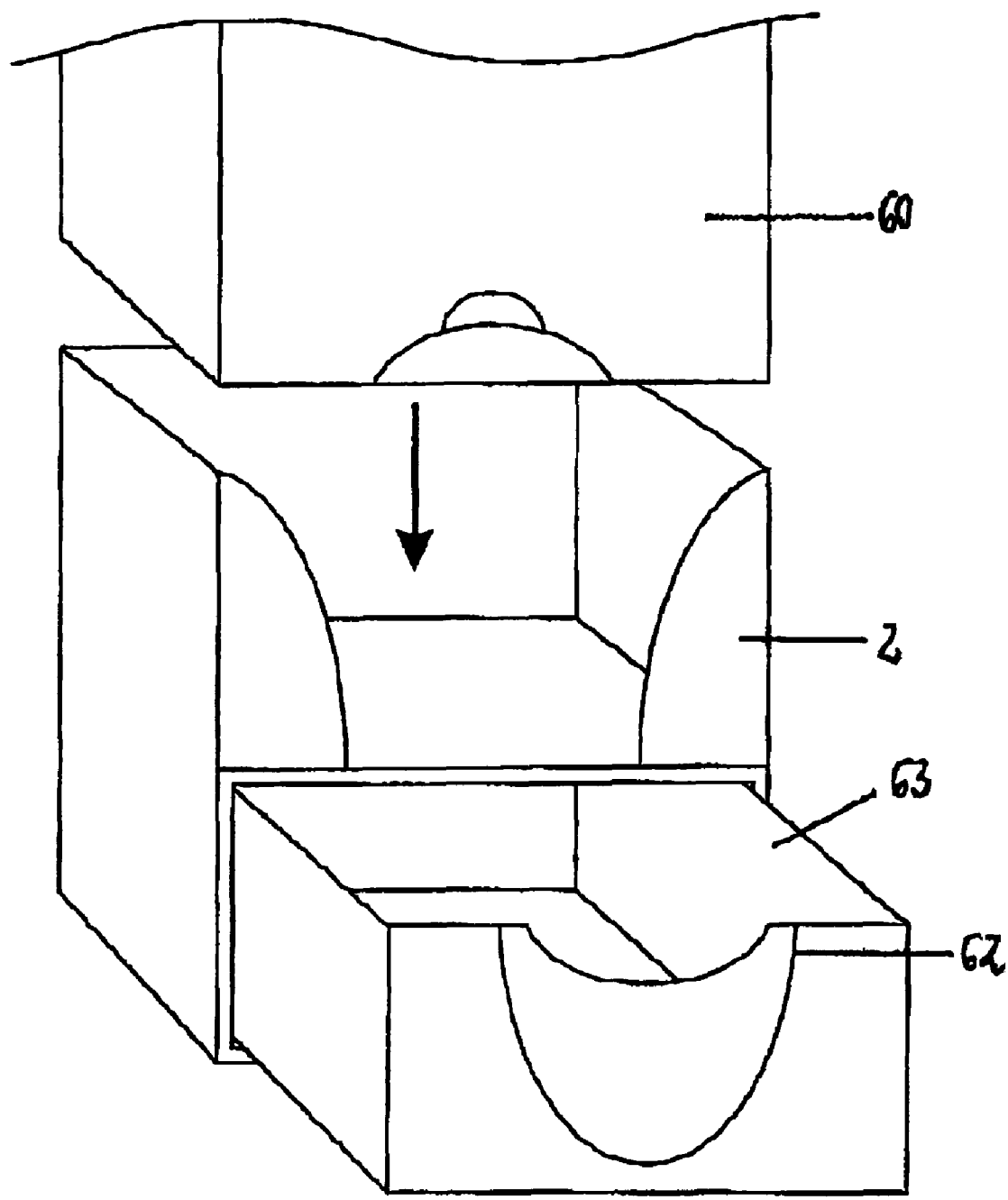
FIG. 6B shows the receptacle according to FIG. 6B with the drawer compartment in open position.

FIGS. 6A and 6B illustrate an embodiment of a receptacle 6b for receiving an article of personal hygiene to be disposed of. In FIG. 6 like features are designated by like reference numerals as in FIGS. 1 to 3. The receptacle 60 is disposed in the outer packing 2 which, on the one hand, serves to take up the receptacle 60 and, on the other hand, may be used to fix the receptacle 60 on a wall, which is why the outer packing 2 also may be referred to as fixture. To this end the outer packing 2 preferably is made of stainless steel or plastics, including fastening means at its rear wall or in the bottom, for instance, in the form of holes through which screws can be passed so that the outer packing 2 may be mounted by peg fastening. A drawer compartment 61 is formed in the outer packing/fixture 2 below the receptacle 60 and may be used as a reservoir for fresh tampons. A front wall 62 of a drawer 63 may be made of transparent material to permit checking of the filling level in the drawer 61.

As shown in FIG. 6B, the receptacle 60 is mounted so as to be releasable from the outer packing 2.

The features of the invention disclosed in the specification above, in the claims and drawing may be significant for implementing the invention in its various embodiments, both individually and in any combination.

What is claimed is:

1. A device for receiving a sanitary tampon to be disposed of comprising:

a sanitary tampon discard unit; and and a sanitary tampon distribution unit;

wherein the sanitary tampon discard unit is comprised of a sidewall assembly, a top wall, an interior partitioning bottom and a bottom wall, wherein a first portion of the sidewall assembly, the top wall and a first surface of the interior partitioning bottom define a first receptacle within the sanitary tampon discard unit for housing a disposed sanitary tampon;

wherein a second portion of the sidewall assembly, a second surface of the interior partitioning bottom and the bottom wall define a storage space adjacent the first receptacle that includes a plurality of empty packings which take up the disposed sanitary tampon, wherein the storage space has a package withdrawal opening in a wall of the second portion of the sidewall assembly that facilitates successive individual withdrawal of the empty packings one after the other and wherein adjacent empty packings of the plurality of packings are separably linked to each other;

wherein the top wall of the first receptacle includes a dump opening and a lid connected thereto in a manner to cover and uncover the dump opening through which a packing containing the disposed sanitary tampon can be thrown into the first receptacle, wherein the dump opening is separate and distinct from the package opening;

wherein the sanitary tampon distribution unit is comprised of a support structure configured with a dispensing receptacle, wherein the support structure is comprised of a sidewall assembly and an discard unit interior support, wherein the sidewall assembly is comprised of opposing first and third sidewalls and opposing second and fourth sidewalls, wherein the discard unit interior support extends laterally into the interior of the support structure side wall assembly and connects to the interior walls of the first, second, third and fourth sidewalls, and wherein a first portion of a sidewall of the support structure sidewall assembly is partially removed so as to expose the withdrawal package opening of the storage space within the sanitary tampon discard unit when the sanitary tampon discard unit is positioned within the sanitary tampon distribution unit and is partially exposed, wherein a first end of the support structure sidewall assembly defines an opening through which the sanitary tampon discard unit passes when positioned on the discard unit support wall, wherein the dispensing receptacle, comprising a dispenser sidewall assembly and dispenser bottom wall, stores fresh hygiene articles and is separate from the first receptacle and the storage space, wherein a bottom portion of the first sidewall of the support structure sidewall assembly is a sidewall of the dispenser sidewall assembly of the dispensing receptacle which is configured as a drawer that moves laterally underneath the discard unit interior support to facilitate removal of fresh articles of personal hygiene.

2. The device as claimed in claim 1, wherein the lid has first and second ends wherein the first end is connected to the top wall of the sanitary tampon discard unit in manner so that the lid may be swung between closed and open positions and wherein the second end of the lid may be releasably connected to to the top wall.

3. The device as claimed in claim 2, wherein the lid has a exterior surface and an interior surface, wherein the interior surface of the lid covers the dump opening when the lid is in a closed position and wherein the top wall includes interior surface of the lid has a raised portion.

4. The device as claimed in claim 2, wherein a fragrant substance is disposed on the lid to produce a smell of freshness.

5. The device as claimed in claim 1, wherein the dump opening is covered by a plurality of strips of resilient material fastened to the interior of the top wall of the sanitary tampon discard unit, wherein the strips are fastened in a manner so that they are overlapping where a slit is formed a cover which is formed with a slit.

6. The device as claimed in claim 5, wherein the cover is defined by strips of resilient material which are fastened to the top wall of the first receptacle and overlap in the area of the slit.

7. The device as claimed in claim 6, wherein the strips are strips of sheet material.

8. The device as claimed in claim 1, wherein the dispenser bottom wall is inclined towards the bottom portion of the first sidewall of the support structure, whereby the empty packings in the dispensing receptacle will slide toward the withdrawal opening to be grasped readily by a user.

9. The device as claimed in claim 1, wherein the sanitary tampon discard unit is made of at least one of cardboard and composite material.

10. The device as claimed in claim 9, wherein the interior walls of the first receptacle of the sanitary tampon discard unit are coated with a material that is impervious to liquid.

11. The device as claimed in claim 1 wherein the plurality of packings are plastic bags.

12. The device as claimed in claim 1, wherein the dump opening is in the top wall of the first receptacle.

13. The device as claimed in claim 1, wherein the dump opening is in a wall of the first portion of the sidewall assembly of the first receptacle.

14. A system for dispensing new and disposing of used sanitary tampons comprising:

a sanitary tampon discard unit; and a sanitary tampon distribution unit configured to hold the sanitary tampon discard unit;

wherein the sanitary tampon discard unit comprises a sidewall assembly, a top wall, an interior partitioning bottom and a bottom wall, wherein a first portion of the sidewall assembly, the top wall and a first surface of the interior partitioning bottom define a discard receptacle for housing discarded sanitary tampons, and wherein a second portion of the sidewall assembly, a second surface of the interior partitioning bottom and the bottom wall define a package receptacle adjacent the discard receptacle for housing a plurality of empty packings, wherein the package receptacle has a package orifice in the second portion of the sidewall assembly that facilitates successive individual withdrawal of the empty packings one after the other from the package receptacle and wherein adjacent empty packings of the plurality of empty packings are separably linked to each other;

wherein the top wall of the discard receptacle has a discard orifice and a dump door connected to the top wall in a manner to cover and uncover the discard orifice, wherein a packing containing a discarded sanitary tampon may be placed in the discard receptacle through the discard orifice, wherein the discard orifice and the package orifice are separate and distinct;

wherein the sanitary tampon distribution unit comprises a support sidewall assembly and a dispensing drawer, wherein the support sidewall assembly includes a discard unit interior support structure, wherein the support sidewall assembly is comprised of opposing first and third sidewalls and opposing second and fourth sidewalls, wherein the discard unit interior support extends laterally across the interior of the support sidewall assembly connecting the interior walls of the first, second, third and fourth sidewalls, and wherein a first portion of a sidewall of the support sidewall assembly is partially removed so as to expose the package orifice of the package receptacle within the sanitary tampon discard unit when the sanitary tampon discard unit is positioned on the discard unit interior support structure within the sanitary tampon distribution unit;

wherein a portion of the support sidewall assembly is a sidewall of the dispensing drawer, wherein the sidewall of the dispensing drawer is connected to a dispensing drawer body that defines a storage area of the dispensing drawer, wherein the support sidewall assembly has a first end and a second end, wherein the second end of the support sidewall assembly defines an opening into which the sanitary tampon discard unit is inserted, wherein the support sidewall assembly includes an interior support structure attached to an interior surface of the support sidewall assembly and positioned above the dispensing drawer, wherein the sanitary tampon discard unit sits on the support structure when positioned inside the opening at the second end of the support sidewall assembly; wherein a portion of the support sidewall assembly has been removed to expose the package orifice of the sanitary tampon distribution unit when the sanitary tampon discard unit sits in the support structure.

15. The device of claim 14 wherein the support structure of the interior surface of the support sidewall assembly comprises a support member extending from the interior surface of the sidewall assembly above the dispensing drawer, wherein the sanitary tampon discard unit sits on the support member when positioned in the opening of the sidewall assembly.

16. The device of claim 14 wherein the support structure of the interior surface of the support sidewall assembly comprises a support wall extending across the interior of the sidewall assembly above the dispensing drawer, wherein the sanitary tampon discard unit sits on the support wall when positioned in the opening of the sidewall assembly.

\* \* \* \* \*